(12) United States Patent
Chang

(10) Patent No.: US 11,064,912 B2
(45) Date of Patent: Jul. 20, 2021

(54) FALL SENSOR

(71) Applicant: Climax Technology Co., Ltd., Taipei (TW)

(72) Inventor: Michael Chang, Taipei (TW)

(73) Assignee: CLIMAX TECHNOLOGY CO., LTD., Taipei (TW)

( * ) Notice: Subject to any disclaimer, the term of this patent is extended or adjusted under 35 U.S.C. 154(b) by 356 days.

(21) Appl. No.: 15/006,405

(22) Filed: Jan. 26, 2016

(65) Prior Publication Data
US 2017/0209077 A1    Jul. 27, 2017

(51) Int. Cl.
*A61B 5/11* (2006.01)
*A61B 5/00* (2006.01)

(52) U.S. Cl.
CPC .......... *A61B 5/1117* (2013.01); *A61B 5/6802* (2013.01); *A61B 5/6822* (2013.01); *A61B 5/7282* (2013.01); *A61B 5/746* (2013.01); *A61B 5/0002* (2013.01); *A61B 2562/0219* (2013.01)

(58) Field of Classification Search
CPC ... A61B 5/1117; A61B 5/6822; A61B 5/7282; A61B 5/6802; A61B 5/746; A61B 2562/0219; A61B 5/0002
See application file for complete search history.

(56) References Cited

U.S. PATENT DOCUMENTS

| | | | | |
|---|---|---|---|---|
| 6,166,644 A * | 12/2000 | Stroda | ................... | A61B 5/1113 340/521 |
| 6,997,882 B1 * | 2/2006 | Parker | ...................... | A61B 5/08 600/301 |
| 8,206,325 B1 * | 6/2012 | Najafi | ................... | A61B 5/1116 600/595 |
| 8,878,889 B1 * | 11/2014 | Kaupp | .................. | H04W 76/50 348/14.02 |
| 2001/0032059 A1 * | 10/2001 | Kelly, Jr. | ............. | A61B 5/0002 702/150 |
| 2007/0118056 A1 * | 5/2007 | Wang | .................... | A61B 5/1116 600/595 |
| 2008/0064375 A1 * | 3/2008 | Gottlieb | .................. | H04W 4/90 455/414.1 |
| 2008/0129518 A1 * | 6/2008 | Carlton-Foss | ......... | G08B 25/10 340/573.1 |
| 2008/0146892 A1 * | 6/2008 | LeBoeuf | ................ | A61B 5/415 600/300 |
| 2008/0200774 A1 * | 8/2008 | Luo | ...................... | A61B 5/4815 600/301 |
| 2009/0203350 A1 * | 8/2009 | Gottlieb | ............. | H04M 1/2749 455/404.1 |

(Continued)

*Primary Examiner* — Sean P Dougherty
(74) *Attorney, Agent, or Firm* — McClure, Qualey & Rodack, LLP

(57) ABSTRACT

A fall sensor coupled to a necklace to detect a fall of a user is provided. The fall sensor includes a first sensing device, a second sensing device, a wireless module and a controller. The first sensing device is coupled to the necklace to detect a tension force of the necklace. The controller is coupled to the first sensing device, the second sensing device and the wireless module. When the first sensing device detects the tension force is changed, the controller activates the second sensing device to confirm whether the user is falling down, and when the user is determined to be fallen down, and the controller outputs an emergency message via the wireless module.

1 Claim, 4 Drawing Sheets

(56) References Cited

U.S. PATENT DOCUMENTS

| | | | |
|---|---|---|---|
| 2009/0292227 A1* | 11/2009 | Scholten | A61B 5/0031 600/595 |
| 2009/0322521 A1* | 12/2009 | Jacobson | H04W 12/0804 340/540 |
| 2010/0286545 A1* | 11/2010 | Wolfe | A61B 5/6833 600/534 |
| 2010/0286567 A1* | 11/2010 | Wolfe | A61B 5/1117 600/587 |
| 2011/0077865 A1* | 3/2011 | Chen | A61B 5/1117 702/3 |
| 2011/0144542 A1* | 6/2011 | Jin | A61B 5/0002 600/595 |
| 2012/0029392 A1* | 2/2012 | Jin | A61B 5/0002 600/595 |
| 2012/0101770 A1* | 4/2012 | Grabiner | A61B 5/1116 702/141 |
| 2012/0259577 A1* | 10/2012 | Ganyi | A61B 5/1117 702/139 |
| 2012/0314901 A1* | 12/2012 | Hanson | A61B 5/0077 382/103 |
| 2013/0054180 A1* | 2/2013 | Barfield | G01P 15/0891 702/138 |
| 2013/0120147 A1* | 5/2013 | Narasimhan | A61B 5/1117 340/573.1 |
| 2014/0276238 A1* | 9/2014 | Osorio | A61B 5/0205 600/595 |
| 2015/0025817 A1* | 1/2015 | Ten Kate | G01L 7/00 702/50 |
| 2015/0123785 A1* | 5/2015 | Haflinger | A61B 5/6831 340/539.11 |
| 2015/0228177 A1* | 8/2015 | Yi | G08B 21/0446 340/573.1 |
| 2015/0279187 A1* | 10/2015 | Kranz | H04M 1/6041 340/539.12 |
| 2016/0038061 A1* | 2/2016 | Kechichian | A61B 5/4035 600/301 |
| 2016/0058330 A1* | 3/2016 | Menzel | A61B 5/747 600/595 |
| 2016/0203692 A1* | 7/2016 | Ten Kate | A61B 5/681 340/573.1 |
| 2016/0275771 A1* | 9/2016 | Visweswara | A61B 5/6822 |
| 2016/0379476 A1* | 12/2016 | Sella | A61B 5/1113 340/539.19 |
| 2017/0228953 A1* | 8/2017 | Lupovici | G07C 9/00896 |

\* cited by examiner

FALL SENSOR

BACKGROUND OF THE INVENTION

Field of the Invention

The present invention relates to a fall sensor and more particularly to a fall sensor with two-step sensing mechanism.

Description of the Related Art

With the growth of the proportion of older people, home care for elderly people has become an important social problem. According to the statistics, falls are a major risk for the elderly people. Once the elderly people fall down, the elderly people may be serious injured, and if the elderly people do not get a timely medical care, the situation may be worse.

BRIEF SUMMARY OF THE INVENTION

One object of the application is to provide a fall sensor without complexity design. Another object of the application provides a fall sensor with a two-step detection mechanism.

In one embodiment, a fall sensor coupled to a necklace to detect a fall of a user is provided. The fall sensor includes a first sensing device, a second sensing device, a wireless module and a controller. The first sensing device is coupled to the necklace to detect a tension force of the necklace. The controller is coupled to the first sensing device, the second sensing device and the wireless module. When the first sensing device detects the tension force is changed, the controller activates the second sensing device to confirm whether the user is falling down, and when the user is determined to be fallen down, the controller outputs an emergency message via the wireless module.

Another embodiment of the invention provides a fall detection method for a fall sensor connecting to a necklace. The method comprises steps of determining whether a tension force of the necklace is changed by a first sensing device; activating a second sensing device by a controller of the fall sensor to execute a confirmation procedure when the tension force of the necklace is changed; outputting an emergency message when the confirmation procedure is passed.

A detailed description is given in the following embodiments with reference to the accompanying drawings.

BRIEF DESCRIPTION OF THE DRAWINGS

The present invention can be more fully understood by reading the subsequent detailed description and examples with references made to the accompanying drawings, wherein.

DETAILED DESCRIPTION OF THE INVENTION

The following description is of the best-contemplated mode of carrying out the invention. This description is made for the purpose of illustrating the general principles of the invention and should not be taken in a limiting sense. The scope of the invention is best determined by reference to the appended claims.

Figure 1:
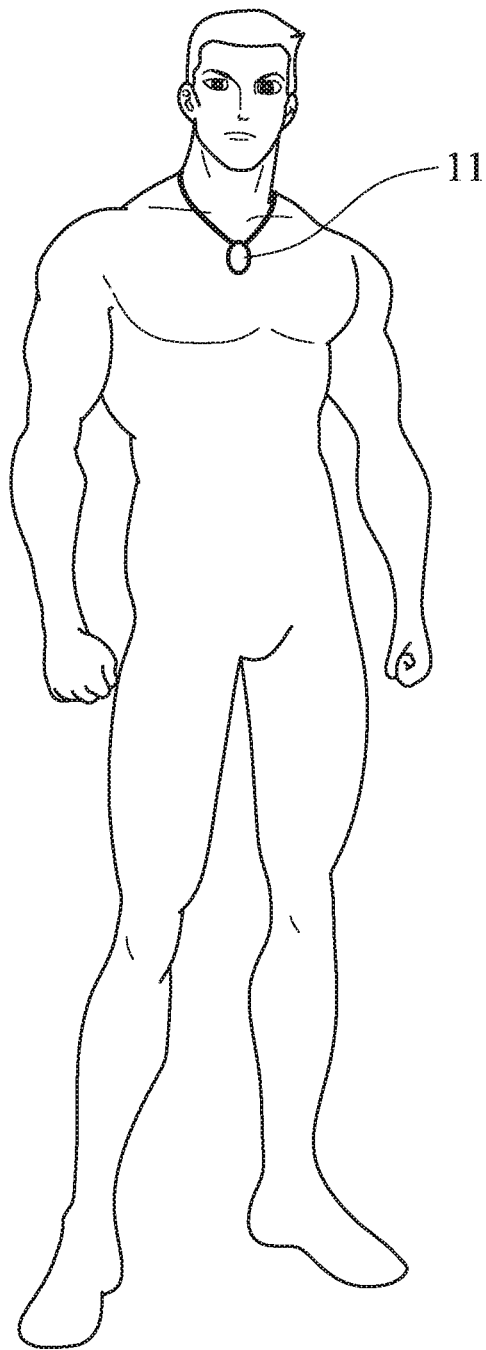
FIG. 1 shows a person wearing the proposed fall sensor.

The innovation provides a fall sensor with a two-step detecting mechanism. Please refer to FIG. 1. FIG. 1 shows a person wearing the proposed fall sensor. When the user wears the fall sensor, the gravity pulls down the fall sensor and a tension force is generated on the necklace. Once the user falls, the fall sensor is at a state of weightlessness, the tension force is disappeared accordingly. Thus, the proposed provides a fall sensor to detect the weightlessness state. Once the weightlessness state is detected, the user may be falling. Therefore, the proposed fall sensor uses a gravity sensor to determine whether the user is falling according to the sensed data. Thus, the proposed innovation uses the phenomenon to achieve the two-step fall detection.

Figure 2:
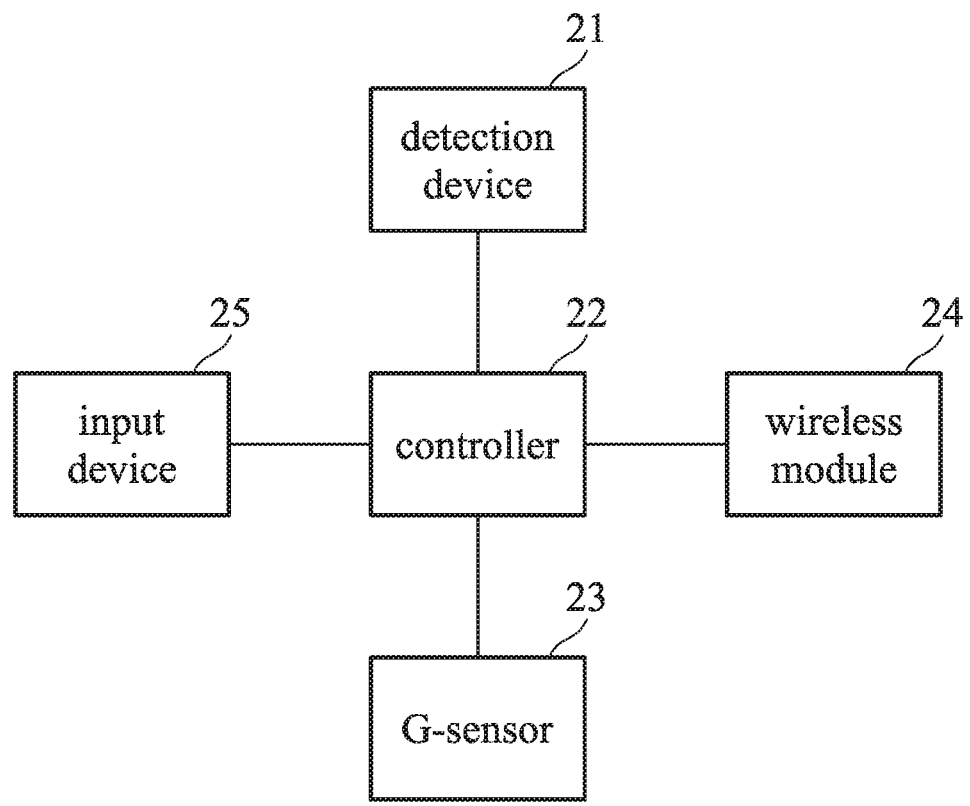
FIG. 2 is a schematic diagram of a fall sensor according to an embodiment of the invention.

FIG. 2 is a schematic diagram of a fall sensor according to an embodiment of the invention. The fall sensor comprises a detection device 21, a controller 22, a G-sensor 23, a wireless module 24 and an input device. The detection device 21 connects to a necklace and detects a tension force of the necklace. Once the detection device 21 detects that the tension force is disappeared, a trigger signal or an interrupt signal is generated to inform the controller 22 that the user wearing the fall sensor may be falling.

Once the controller 22 receives a detection result indicating that the user may fall from the detection device 21, the controller 22 activates the G-sensor 23 to determine whether the user is falling. In one embodiment, the G-sensor 23 may be a gyro sensor, an accelerometer or a tri-axis accelerometer. In another embodiment, when the detection device 21 determines that the user may be falling, the detection device 21 transmits a signal to the G-sensor 23 directly, and when the G-sensor 23 receives the signal, the G-sensor 23 senses data and generates a sensing result to determine whether the user is falling according to the sensing result. When the G-sensor 23 determines the user is falling, the G-sensor 23 informs the controller 22, and the controller 22 controls the wireless module 24 to transmit an emergency message or call to ask for help.

In another embodiment, the G-sensor 23 only transmits the sensed data to the controller 22, and the controller 22 determines whether the user is falling according to the sensed data. Once the controller 22 determined the user is falling, the controller 22 controls the wireless module 24 to transmit an emergency message or call to ask for help. Furthermore, once the user feels uncomfortable, the user can send a message for help by the input device 25. The input device 25, or called as an emergency button, comprises at least one button, switch or other similar means. When receive an input signal from the input device 25, the controller 22 controls the wireless module 24 to transmit an emergency message or call to ask help. In another embodiment, to avoid inadvertently touch of the input device 25, the controller 22 determines whether a duration of the input signal generated by the input device 25 exceeds a predetermined threshold, and the controller 22 controls the wireless module 24 to transmit an emergency message or call to ask help only when the duration of the input signal exceeds the predetermined threshold. In one embodiment, the predetermined threshold may be 1-3 second.

According to the described paragraphs, it is obviously that the proposed fall sensor provides a two-step detection mechanism by using the detection device 21 and the G-sensor 23. The detection device 21 generates a detection result according to a change of the tension force of the necklace. Once the change of the tension force matches to a predetermined situation, the detection result or a trigger signal is then transmitted to the controller 22 to confirm whether the user is falling down. The detection device 21 can be implemented by any kind of means which can detect the tension force of the necklace. For example, the detection device 21 comprises a resistance detection device or circuit, and a conduction wire is embedded inside the necklace. The resistance of the conduction wire is varied according to the length of the conduction wire and the conduction wire is malleable. Therefore, a reference resistor is embedded in the resistance detection device to check whether the tension force of the necklace disappears. The resistance of the reference resistor indicates a normal condition. In one embodiment, when the detected resistance of the conduction wire and the resistance of the reference resistor are different, the detection result triggers the controller 22 to confirm whether the user is falling down. In another embodiment, only when a difference between the detected resistance of the conduction wire and the resistance of the reference resistor exceeds a threshold, the detection result triggers the controller 22 to confirm whether the user is falling down.

The detection device 21 further comprises a comparator to compare the detected resistance of the conduction wire and the resistance to output a comparison result. The comparison result may be a voltage value or a digital value, such as 0 or 1. In one embodiment, the detection 21 generates the detection result according to the compared result and transmits the detection result to the controller 22. In another embodiment, the output of the comparator is directly connected to the controller 22 and the compared result is the described detection result.

In another embodiment, the detection device 21 comprises a mechanical spring and a force detection device or circuit. The force detection device detects a force change or a deformation of the mechanical spring. Once the change of the mechanical spring exceeds a threshold, the detection device 21 transmits the detection result to the controller 22. When the controller 22 receives the detection result indicating that the user may be falling, the controller 22 confirms whether the user is fall according to sensing data from the G-sensor 23. In another embodiment, the force detection device can be replaced by a length detection device to detect a deformation of the mechanical spring. Once the deformation of the mechanical spring exceeds a threshold, the detection device 21 transmits the detection result to the controller 22, and the controller 22 confirms whether the user is fall according to sensing data from the G-sensor 23.

In another embodiment, the detection device 21 is a switch directly connected to a pin of the controller 22. The switch is turned off by the necklace due to the gravity in a normal condition. When the user falls, the switch is turned on, and a logic level of the pin of the controller 22 is changed. The controller 22 determines that the user may be falling, and activates the G-sensor 23 to confirm whether the user is falling according to sensing data from the G-sensor 23.

Although the detection device 21 is illustrated with several specific apparatus above, but the detection device 21 is not limited thereto.

When the controller 22 confirms whether the user is falling according to the sensing data from the G-sensor 23, a confirmation procedure is executed. Only when the confirmation procedure is passed, the user is determined to be fallen down. The confirmation procedure comprises determination of three phases with the following states:

(1) stall state or weightlessness state
(2) strike state
(3) static state

The G-sensor 23 can detect a gravity value (G value) in phase 1, and when the detected G value is 0, the controller 22 determines that the fall sensor may be at the weightless state. Then, the controller 22 determines whether duration of the weightless state is greater than a predetermined duration, such as 0.1~0.5 second. Once the duration is greater than the predetermined duration, the controller 22 determines the fall sensor is at the weightless state.

Then, the controller 22 determines in phase 2 whether the strike state is detected within a predetermined time after the weightless state is detected. If the user falls down to the ground, the G-sensor 23 detects a strike force and the sensed G value may be greater than a predetermined value, such as 3 G. Thus, the strike state is determined according to the sensing G value from the G-sensor 23.

When the controller 22 determines in phase 2 that the fall sensor is at the strike state, the controller 22 further determines in phase 3 whether the static state is matched according to the sensing data from the G-sensor 23. If the sensing data from the G-sensor 23 does not change for a predetermined duration, such as 3 seconds, the controller 22 determines that the fall sensor is at the static state and transmits the emergency message or call to ask help. In one embodiment, the fall sensor is compatible with a monitor console and the controller 22 sends a request to the monitor console via the wireless module 24 and the monitor console transmits the emergency message or call to a service server to ask help.

In another embodiment, the G-sensor 23 further determines a distance that the user falls down in phase 2 for determining the static state. The distance is determined according to acceleration speed in three axes, X, Y and Z. An example of the distance determining equation is provided:

$$\vec{a}=a_x\hat{x}+a_y\hat{y}+a_z\hat{z}$$

$$\vec{D}=\int \vec{a}\,d^2t$$

In another embodiment, the static state can be determined by comparing the sensing data when the G-sensor 23 is activated and a current sensing data.

Figure 3:
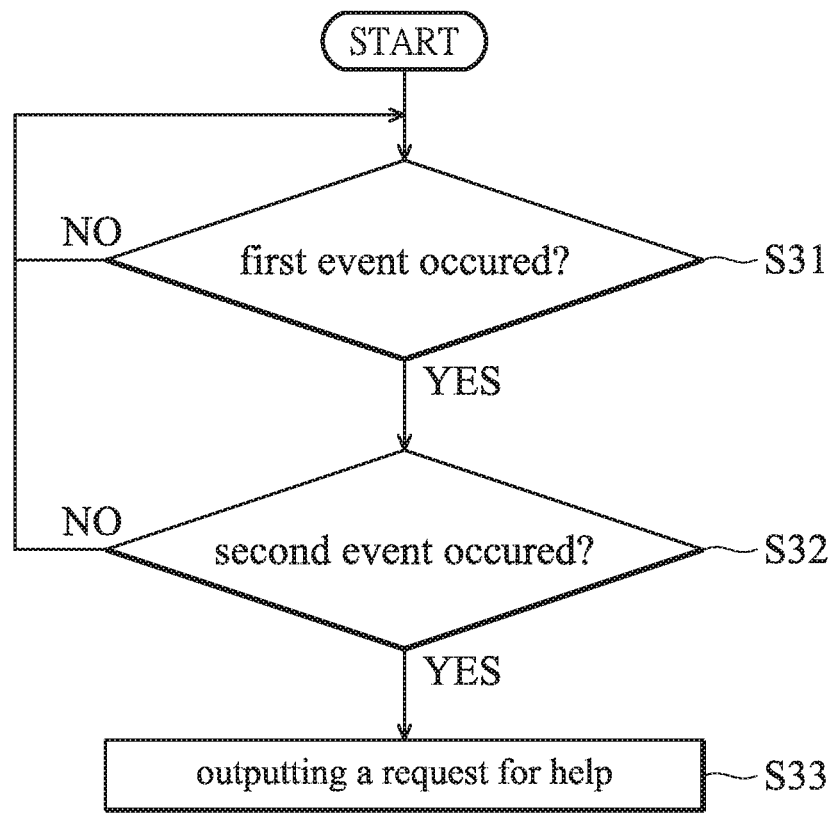
FIG. 3 is a fall detection method according to an embodiment of the invention.

FIG. 3 is a fall detection method according to an embodiment of the invention. In this embodiment, the fall detection method is implemented by the fall sensor illustrated in FIG. 2. In step S31, a controller of the fall sensor determines whether a first event occurred. The first event is determined according to a tension force of a necklace connected to the fall sensor. Once the tension force is changed or disappeared, the controller determines that the first event is occurred. In step S32, the controller determines whether a second event is occurred. The second event is determined according to sensing data from a G-sensor. The detail of the second event determination can be referred to the operation above and not discussed here for briefly. When the second event is occurred, it means that the user is fallen down, and the controller of the fall sensor output a request for help. Note that a time duration between the step S31 and the step S32 is less than a predetermined period, such as 3-10 seconds. When the first event is occurred and the second event is not occurred within the predetermined period, the user will not be determined fallen down, and the procedure of the method returns to step S31.

Figure 4:
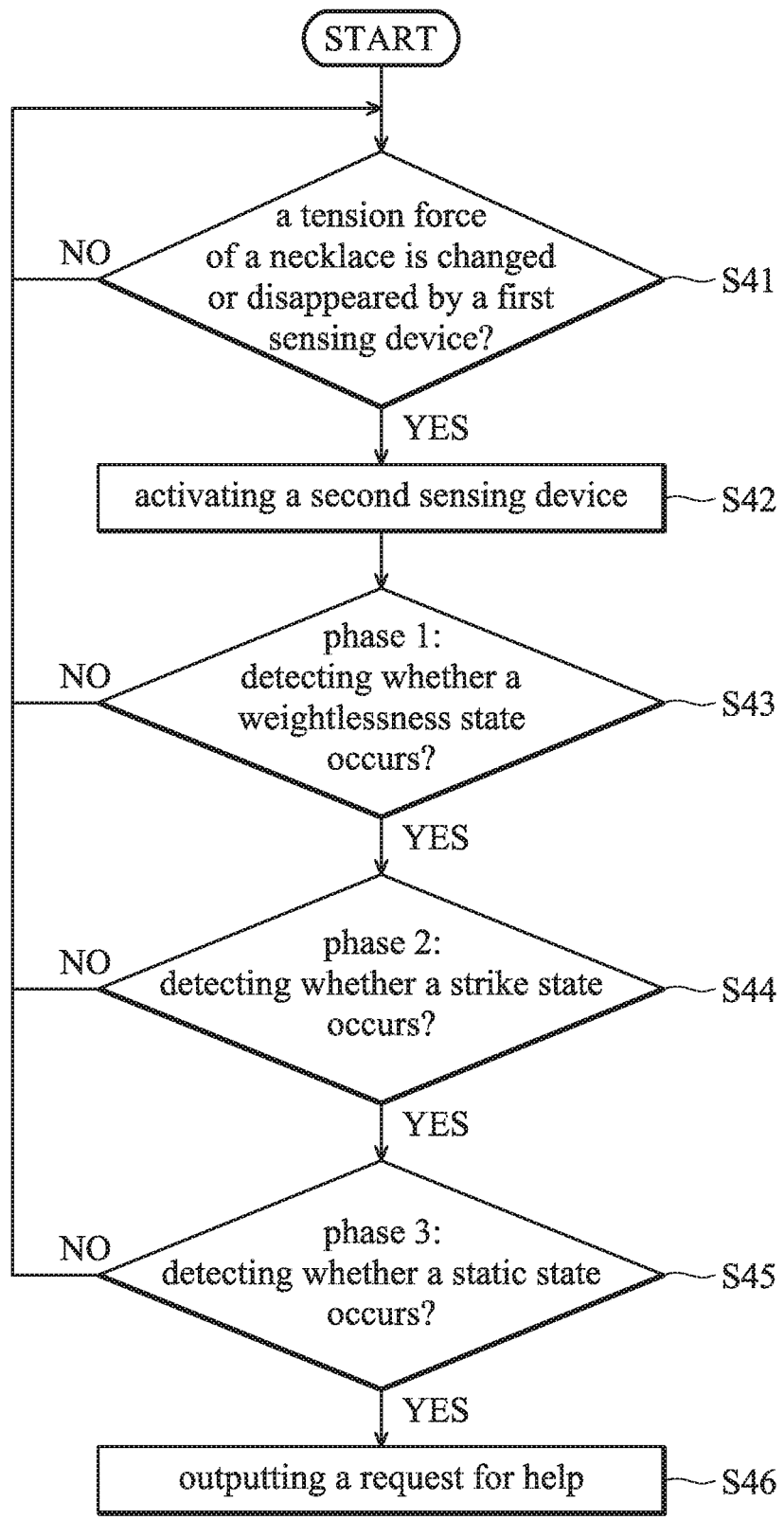
FIG. 4 is a fall detection method according to another embodiment of the invention.

FIG. 4 is a fall detection method according to another embodiment of the invention. In this embodiment, the fall detection method is implemented by the fall sensor illustrated in FIG. 2. In step S41, a first sensing device, such as the detection device 21 in FIG. 2, detects whether a tension force of a necklace is changed or disappeared. If yes, it indicates that the user wearing the fall sensor may fall down, and a step S42 of phase 1 is executed. If not, the procedure returns to the beginning of the method.

In step S42, a controller of the fall sensor activates a second sensing device, such as the G-sensor 23 in FIG. 2. In step S43 of phase 1, the controller or the second sensing device determines whether a weightlessness state occurs? If not, the procedure returns to the beginning of the method. If yes, phase 2 with step S44 is executed. In step S44, the controller or the second sensing device determines whether a strike state occurs? If not, the procedure returns to the beginning of the method. If yes, phase 3 with step S45 is executed. In step S45, the controller or the second sensing device determines whether a static state occurs? If not, the procedure returns to the beginning of the method. If yes, step S46 is executed. In step S46, the user is determined to be fallen down and an emergency message is output for asking help. In this embodiment, the detail of 3 phases with steps S43~S45 can be referred to the description of FIG. 2 and not discussed here for briefly.

While the invention has been described by way of example and in terms of the preferred embodiments, it is to be understood that the invention is not limited to the disclosed embodiments. To the contrary, it is intended to cover various modifications and similar arrangements (as would be apparent to those skilled in the art). Therefore, the scope of the appended claims should be accorded the broadest interpretation so as to encompass all such modifications and similar arrangements.

What is claimed is:

1. A fall sensor detecting a fall of a user, comprising:
a first sensing device coupled to a necklace;
wherein the first sensing device detects a tension force of the necklace;
a second sensing device comprising a G-force sensor;
a wireless module;
a controller coupled to the first sensing device, the second sensing device and the wireless module; and
an emergency button and when the controller determines that the emergency button is pressed for a predetermined duration, the controller outputs an emergency message via the wireless module;
wherein when the first sensing device detects the tension force is changed, the controller activates the second sensing device to confirm whether the user is falling down, and when the user is determined to be fallen down, the controller outputs the emergency message via the wireless module;
wherein the second device confirms whether the user is falling down by a confirmation procedure that comprises:
determining whether a weightlessness state occurs;
determining whether a strike state occurs;
determining whether a static state occurs; and
when the weightlessness state, the strike state and the static state occurs sequentially, the user is determined to be fallen down, the controller outputs the emergency message via the wireless module;
wherein the first sensing device comprises a resistance sensing device and a conductive line is embedded in the necklace, and the first sensing device determines whether the tension force is changed according to a capacitance of the conductive line;
wherein when the first sensing device detects that a tension force has disappeared, a trigger signal or an interrupt signal is generated to inform a controller, and the controller activates the G-sensor to determine whether the user is falling; wherein when the G-sensor determines that the user is falling, the G-sensor informs the controller, and the controller controls a wireless module to transmit an emergency message; and
wherein when a detected resistance of the conductive line and a resistance of a reference resistor are different, a detection result triggers the controller to confirm whether the user is falling down.

* * * * *